United States Patent [19]

Dönges et al.

[11] Patent Number: 4,748,645
[45] Date of Patent: May 31, 1988

[54] DEVICE FOR PRODUCING X-RAY PICTURES OF BODIES

[76] Inventors: Gerhard Dönges, Am Markt 1, Kemel 1, Fed. Rep. of Germany, 6209; Cornelius Koch, Leberberg 20, Wiesbaden, Fed. Rep. of Germany, 6200

[21] Appl. No.: 598,294
[22] PCT Filed: Aug. 10, 1983
[86] PCT No.: PCT/EP83/00213
§ 371 Date: Apr. 2, 1984
§ 102(e) Date: Apr. 2, 1984

[30] Foreign Application Priority Data

Aug. 11, 1982 [DE] Fed. Rep. of Germany ....... 3229914

[51] Int. Cl.⁴ .......................... A61B 6/00; H05G 1/64
[52] U.S. Cl. ...................................... 378/19; 378/99; 358/111
[58] Field of Search .................. 378/147, 149, 19, 99, 378/146; 250/366, 363 SE; 358/111

[56] References Cited

U.S. PATENT DOCUMENTS 3,973,128 8/1976 LeMay ................................. 378/11
4,129,783 12/1978 Houston ............................... 378/19
4,160,167 7/1979 Weiss et al. ......................... 250/366
4,160,911 7/1979 Hounsfield ........................... 378/19
4,187,430 2/1980 Schmidt ............................... 378/19
4,193,001 3/1980 Liebetruth et al. .................. 378/19
4,394,063 7/1983 Weiss et al. ........................ 350/3.75
4,504,962 3/1985 Moore ................................. 378/19

FOREIGN PATENT DOCUMENTS 2430021 1/1976 Fed. Rep. of Germany .
2814242 10/1979 Fed. Rep. of Germany ........ 378/19
0086745 5/1982 Japan ................................... 378/19

Primary Examiner—Janice A. Howell

[57] ABSTRACT

X-ray pictures of bodies are produced by a point X-ray source by providing measuring points in a linear detector array for the local intensity of the X-rays; their measured values control the brightness in picture elements of a monitor. All embodiments of the linear detector array deviating from a circular arc about the X-ray generator result in nonlinear distortion. The nonlinear distortions are compensated by a corresponding arrangement of the measuring points. The invention can be used for checking any object.

4 Claims, 2 Drawing Sheets

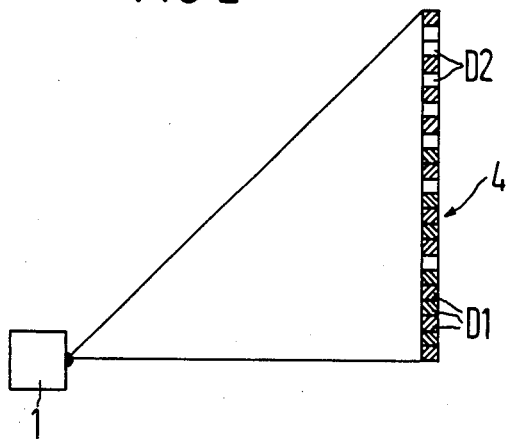
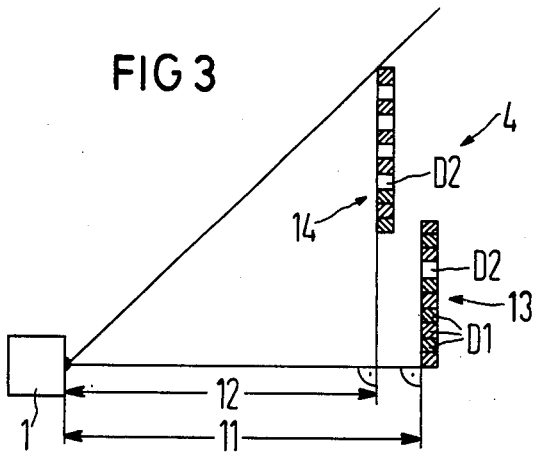

DEVICE FOR PRODUCING X-RAY PICTURES OF BODIES

BACKGROUND OF THE PRIOR ART

The present invention relates to a device for producing X-ray pictures of bodies or objects that are moved in a test channel, relative to an X-ray generator.

Devices of this general type are known, wherein rows of detectors are linear and are disposed along a wall of a rectangular testing chamber. Such detector rows result in nonlinear distortion of the distances which become larger with increasing distance from the perpendicular, from the X-ray source to the detector row.

The object underlying the present invention consists of compensating the nonlinear distortions in a device of this type, wherein conventional components and equipment are to be employed to the greatest possible degree.

SUMMARY OF THE INVENTION

The invention is based on the knowledge that the change of the angle of the incident X-ray to the perpendicular from the X-ray generator to the straight line going through the two adjacent measurement points governs the degree of the nonlinear distortion. This relationship applies to straight detector rows as well as to detector rows which are curved in any manner and deviate from the shape of a circular arc, the center of which is located in the X-ray generator. Discontinuities in the profile of the detector rows also do not disturb this relationship.

Using the change of the distance between the measuring points in this way, has the further advantage of permitting all other components and equipment, especially also the picture monitor, to be commercially available components.

It follows that the distance between two adjacent measuring points is proportional to the reciprocal value of the cosine of the angle of the incident X-ray beam to the perpendicular from the X-ray generator to the straight line through two adjacent measuring points and this insight makes it possible to determine the distances between adjacent measuring points independently of the shape of the row of the detectors. The profile of the detector row may also include discontinuities.

The design rule to be used can be written in the form of a formula as follows:

$$A_i = A_0 \frac{r_i}{\cos \alpha_i}$$

wherein $A_i$ is the distance between adjacent measuring points having the numbers $i$ and $i+1$. The distance $A_0$ can be chosen according to the desired resolution or, in the case of a given number of picture elements per line on the picture monitor, according to the dimensions of the equipment. For $r_i=1$, it indicates the spacing of two measuring points if the perpendicular from the X-ray generator to the connecting line through the two measuring points intersects the connecting line.

Advantageously, detector rows are arranged along all walls of the test channel accessible to the X-rays after transversing the test space, and are adapted to the shape thereof.

Advantageously, the device includes detector rows or arrays, which include detectors at regular spacings, not all the detectors are employed as measuring points for generating picture elements and their mutual spacing is determined by an appropriate selection of the type of detectors employed. This embodiment has the advantage of permitting detector arrays prefabricated in quantity with constant detector spacings to be used. Several prefabricated detector arrays can be arranged in tandem and used for displaying one line for reproduction on the monitor.

In summary, the device for producing X-ray pictures of bodies, in which the bodies can be moved in a test channel relative to an X-ray generator, includes a linear detector array disposed opposite the X-ray generator. The detector measures the intensity of the incoming X-radiation and feeds the measured values to a device for generating a picture composed of individual picture elements, wherein the brightness of every picture element of the visible picture is adjusted in accordance with a measured value of the linear detector array. At least one measuring point has a distance from the X-ray generator which is different from the distance of the adjacent measuring points in the detector array; and the picture elements of the visible picture have the same spacings relative to the respective adjacent picture elements; the mutual spacings of adjacent measuring points in the detector array are made proportional to the product of the distance ($r_i$) from the X-ray generator and the reciprocal value of the cosine of the angle ($\delta_i$) between the incident X-ray and the perpendicular from the X-ray generator to a straight connecting line through the two adjacent measuring points.

In accordance with another feature of the invention the device includes one or more linear detector arrays, so that the detector arrays include detectors that are equally spaced apart in the array but such that not all the detectors are used.

In accordance with an additional feature of the invention, there is included a plurality of detector arrays that are disposed along all the walls of the test space and are adapted to the shape of the walls.

BRIEF DESCRIPTION OF THE DRAWING

FIG. 2 shows schematically an embodiment example of a device according to the invention;

FIG. 3 shows an embodiment example having a detector array with two offset parts.

DESCRIPTION OF THE PREFERRED EMBODIMENTS

Figure 1:
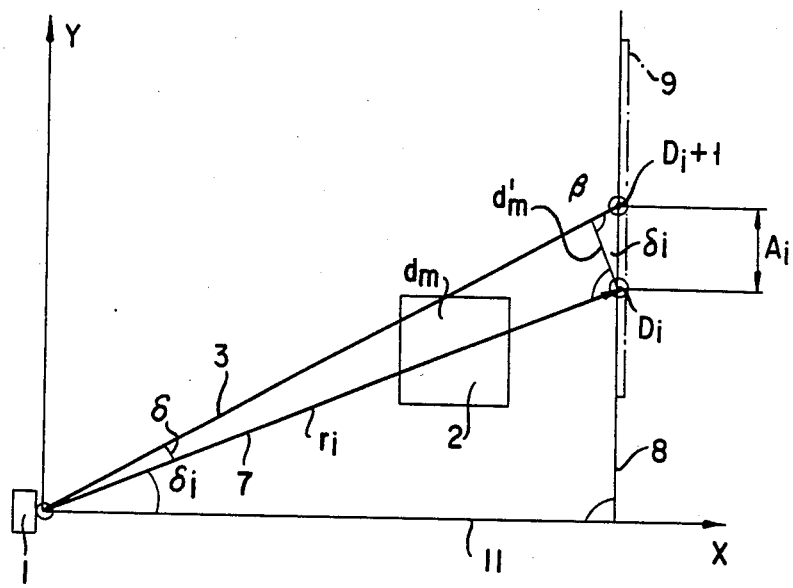
FIG. 1 shows schematically the method of the correction of the nonlinear distortions.

As seen in FIG. 1, X-rays 3 and 7 emanate from an X-ray generator 1. The X-ray generator 1 is to be considered a point source of X-radiation. After passing through the body 2, an X-ray reaches the X-ray detector $D_i$ at the distance $r_i$ from the generator. The X-ray 7 forms an angle $\delta_i$ with the perpendicular from the X-ray generator 1 to the straight connecting line 8 through the X-ray detectors $D_i$ and $D_{i+1}$.

The differential region $d_m$ of the body 2 is imaged on the surface element $d'_m$ without nonlinear distortion. The deviation of the angle $\alpha i$ of the ray 3 to the surface element $d'_m$ with the perpendicular 11 produces no nonlinear distortion if the angle $\delta$ between adjacent X-rays 3 and 7 is constant.

The surface element $d'_m$ forms the angle $\alpha_i$ with the detector line 9. The distance $A_i$ between the detector $D_i$ and the detector $D_{i+1}$ is proportional to the reciprocal value of $\cos\alpha_i$. In addition, $A_i$ is proportional to the distance $r_i$ of the detector $D_i$ from the X-ray generator 1. From this follows the formula $$A_i \sim r_i/\cos\alpha_i.$$

Advantageously, an $A_0$ value is applied as a fixed proportionality factor which represents the desired distance for $r_i=1$ and the angle $\alpha_i=0$. The angle $\delta$ between the X-rays 3 and 7 is automatically taken into consideration here. The location of the measuring points on detector lines of any shape is determined graphically in a simple manner by drawing a circle with the radius 1 about the X-ray generator, by determining, starting with a ray from the X-ray generator to a first measuring points, the direction of the ray to the next measuring point by applying the proportionality factor $A_0$ and by extending the ray to the detector line 9. The point of intersection represents the new measuring point. If the constant angle to be covered is determined, the corresponding angular range of the unit circle can also be divided by the given number of picture element spacings. The rays through the points on the unit circle generated in this way directly yield the location of the measuring points on the detector lines. FIGS. 2 and 3 show a prefabricated linear detector array 4 having X-ray detectors D1, D2 which are disposed in the detector array at equal mutual spacings. The detectors D1 shown with section lines are used as measuring points. Due to the chosen selection of the detectors D1, linearization of the picture on the monitor according to the invention is approximately achieved. Prefabricated and therefore inexpensive detector arrays can be used, and the selection of the detectors D2 used as measuring points can be matched to the respective equipment without the need for changing the linear detector array 4.

The embodiment example of FIG. 3 shows the use of a linear detector array 4 which is composed of two offset smaller sections 13, 14 and therefore shows a discontinuity. The section 14 is shifted toward the X-ray generator 1, so that a smaller number of unused detectors D2 is required than in the example of FIG. 2, where the parts relatively far removed from the X-ray generator 1 already contain relatively many unused detectors D2. This example is advantageous particularly for the testing of objects which are smaller in their upper part than in their lower part.

The equation $A_i = A_0 \cdot r_i/\cos\alpha_i$ applies to the two sections 13, 14 of the linear detector array 4. For each of the straight parts 13 and 14 of the detector line 4, the perpendiculars 11 and 12 on the straight line determined by the sections 13 and 14 must be taken as the basis for determining the distances $A_i$ seen in FIG. 1. The perpendiculars 11 and 12 coincide in their direction in the example shown and are advantageously located in the lower boundary of the test space.

Figure 4:
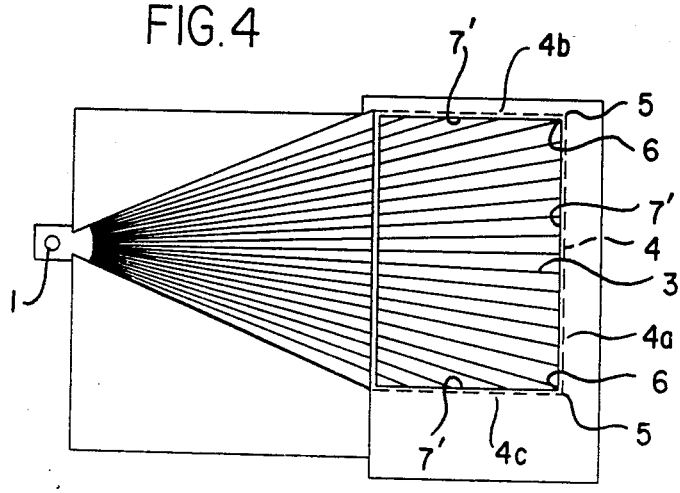
FIG. 4 shows an embodiment example having a detector array following the contour of the test chamber.

FIG. 4 shows the X-ray generator 1 irradiating a channel 3 of rectangular cross-section having inner surfaces joined at the corners 6 and having linear detector arrays 4 covering the outer sides of the surfaces 7. The arrays 4 are divided into sections 4a, 4b and 4c that are joined at the corners 5.1.

Independently of the form of the linear detector arrays, an image without the disturbing nonlinear distortions can always be obtained with the design according to the invention on a commercially available monitor with equal line spacings. Adaption of the spacings to different embodiments of the device is possible, for instance, to different distances from the linear detector array to the X-ray generator.

With this embodiment, a simple design of the driving circuits is achieved by modulating the sampling frequency in such a way that the total time for one complete scan of all detector arrays remains unchanged.

Instead of the linear detector arrays with equal spacings between the individual detectors D1, D2 detector arrays without unused detectors D2 can also be used, if the used detectors D1 are arranged at different mutual spacings which correspond to the mentioned equation for $A_i$.

We claim:

1. Device for producing X-ray pictures of bodies, comprising a test channel in which the bodies can be moved; an X-ray generator disposed in the channel; a linear detector array disposed at a side of the bodies facing away from the X-ray generator for measuring the intensity of the oncoming x-radiation, a device connected to said linear detection array for generating a picture composed of individual picture elements from measured values of the X-ray intensity fed thereto from the linear detection array, every picture element of the picture being adjusted in brightness in accordance with a respective measured value of the linear detector array, at least one measuring point at which a respective measured value is determined being spaced a distance from the X-ray generator which is different from that of others of said measuring points located adjacent said one measuring point in said detector array; each of said picture elements being spaced equally relative to the respective adjacent picture elements of the picture; and mutual spacings between two adjacent measuring points in the detector array being proportional to the product of the distance between one of said measuring points and the X-ray generator and the reciprocal value of the cosine of an angle between the incident X-ray and a perpendicular from the X-ray generator to a straight connecting line through the two adjacent measuring points.

2. Device according to claim 1, including a plurality of said linear detector arrays; detectors included in the detector arrays having equal mutual spacings; and having unused detectors between the detectors used as measuring points for generating picture elements; and wherein the mutual distance between detectors used as measuring points is determined by an appropriate selection of the detectors.

3. Device according to claim 1, comprising at least one detector array disposed along all walls accessible to the X-rays after passing through the test space, and conformed to the shape of the walls.

4. Device according to claim 1, wherein the distance between the measuring points is selected according to the equation $$A_i = A_0 r_i/\cos\alpha_i,$$

wherein $A_i$ is the distance between adjacent measuring points $D_i$, $A_0$ is a scale factor, $r_i$ is the distance from the X-ray generator to the measuring point $D_i$, and the angle $\delta_i$ is the angle between the X-ray incident to the measuring point and the perpendicular from the X-ray generator onto a line through adjacent measuring points.

* * * * *